US011257211B2

(12) United States Patent
Igarashi

(10) Patent No.: US 11,257,211 B2
(45) Date of Patent: Feb. 22, 2022

(54) MEDICAL IMAGE PROCESSING APPARATUS, MEDICAL IMAGE PROCESSING SYSTEM, AND MEDICAL IMAGE PROCESSING METHOD

(71) Applicant: CANON MEDICAL SYSTEMS CORPORATION, Otawara (JP)

(72) Inventor: Takuma Igarashi, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 193 days.

(21) Appl. No.: 16/598,540

(22) Filed: Oct. 10, 2019

(65) Prior Publication Data

US 2020/0118265 A1    Apr. 16, 2020

(30) Foreign Application Priority Data

Oct. 10, 2018    (JP) .............................. JP2018-191547

(51) Int. Cl.

| G06K 9/00  | (2006.01) |
| G06Q 10/00 | (2012.01) |
| G06T 7/00  | (2017.01) |
| A61B 5/055 | (2006.01) |
| G16H 30/20 | (2018.01) |
| A61B 5/00  | (2006.01) |
| G16H 30/40 | (2018.01) |
| A61B 6/00  | (2006.01) |
| A61B 8/08  | (2006.01) |

(52) U.S. Cl.
CPC ............ *G06T 7/0012* (2013.01); *A61B 5/055* (2013.01); *A61B 5/7207* (2013.01); *G16H 30/20* (2018.01); *G16H 30/40* (2018.01); *A61B 6/466* (2013.01); *A61B 8/483* (2013.01); *A61B 8/5215* (2013.01)

(58) Field of Classification Search
USPC ........ 382/100, 103, 106, 128–132, 155–156, 382/168, 173, 181, 190, 199, 209, 217, 382/219, 254, 286–291; 705/2; 378/4, 378/21
See application file for complete search history.

(56) References Cited

U.S. PATENT DOCUMENTS

| 2008/0292194 | A1* | 11/2008 | Schmidt .................... G06T 7/11 |
|              |     |         | 382/217 |
| 2010/0250275 | A1* | 9/2010  | Sakagawa ................ A61B 6/00 |
|              |     |         | 705/2 |
| 2019/0343477 | A1* | 11/2019 | Wang ...................... G06T 7/136 |
| 2020/0074224 | A1* | 3/2020  | Hayashi ............... G06K 9/6253 |
| 2020/0085382 | A1* | 3/2020  | Taerum .................... G06T 7/30 |

FOREIGN PATENT DOCUMENTS

| JP | 2009-113717 A | 5/2009 |
| JP | 2015-194927 A | 11/2015 |

\* cited by examiner

*Primary Examiner* — Seyed H Azarian
(74) *Attorney, Agent, or Firm* — Oblon, McClelland, Maier & Neustadt, L.L.P.

(57) ABSTRACT

A medical image processing apparatus according to an embodiment includes a processing circuit. The processing circuit specifies teaching data used for generation of a learned model. The processing circuit performs image analysis with respect to pieces of collected medical image data. The processing circuit extracts medical image data having an attribute common to the teaching data of the learned model from the pieces of medical image data based on an analysis result of the image analysis, as a candidate of the teaching data of the learned model.

11 Claims, 5 Drawing Sheets

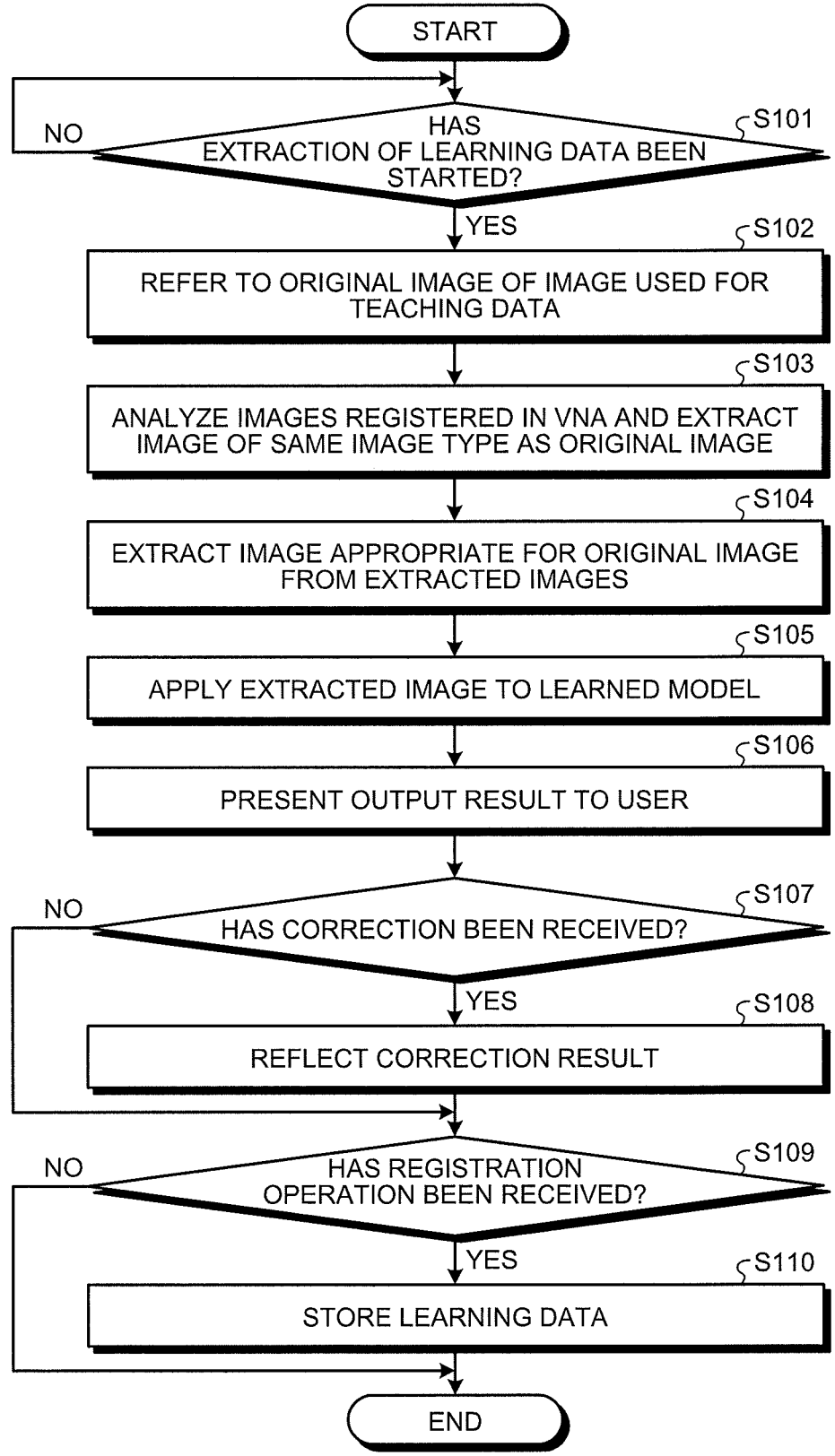

MEDICAL IMAGE PROCESSING APPARATUS, MEDICAL IMAGE PROCESSING SYSTEM, AND MEDICAL IMAGE PROCESSING METHOD

CROSS-REFERENCE TO RELATED APPLICATIONS

This application is based upon and claims the benefit of priority from Japanese Patent Application No. 2018-191547, filed on Oct. 10, 2018; the entire contents of which are incorporated herein by reference.

FIELD

Embodiments described herein relate generally to a medical image processing apparatus, a medical image processing system, and a medical image processing method.

BACKGROUND

Conventionally, a learned model is generated by using pieces of medical image data collected by a medical image diagnostic device and teaching data acquired from the pieces of medical image data as learning data. For generation of such a learned model, for example, appropriate learning data is extracted and used from plural pieces of medical image data.

BRIEF DESCRIPTION OF THE DRAWINGS

FIG. 5 is a flowchart illustrating a processing procedure performed by the medical image processing apparatus according to the present embodiment.

DETAILED DESCRIPTION

According to an embodiment, a medical image processing apparatus includes processing circuitry. The processing circuitry is configured to specify teaching data having been used for generation of a learned model. The processing circuitry is configured to perform image analysis with respect to pieces of collected medical image data. The processing circuitry is configured to extract medical image data having an attribute common to the teaching data of the learned model from the pieces of medical image data based on an analysis result of the image analysis, as a candidate of the teaching data of the learned model.

Embodiments of a medical image processing apparatus, a medical image processing system, and a medical image processing method will be described below in detail with reference to the accompanying drawings. The medical image processing apparatus, the medical image processing system, and the medical image processing method according to the present application are not limited to the embodiment described below.

Embodiment

Figure 1:
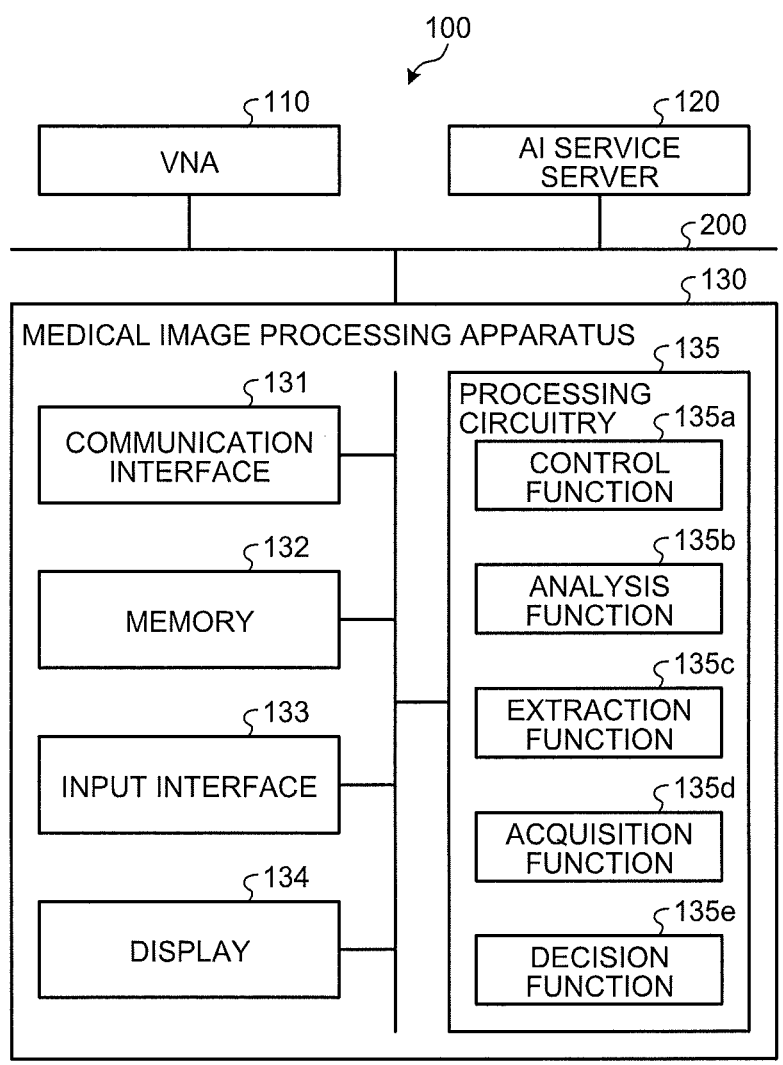
FIG. 1 is a diagram illustrating an example of a configuration of a medical image processing system according to the present embodiment.

FIG. 1 is a diagram illustrating an example of a configuration of a medical image processing system 100 according to the present embodiment. As illustrated in FIG. 1, the medical image processing system 100 according to the present embodiment includes, for example, a VNA (Vendor Neutral Archive) 110, an AI (Artificial Intelligence) service server 120, and a medical image processing apparatus 130. The respective systems and respective apparatuses are connected communicably with each other via a network 200.

The VNA 110 collectively manages various types of medical information. Specifically, the VNA 110 manages a system and data with a unique standard for each diagnosis and treatment department in a hospital. For example, the VNA 110 receives medical image data in a DICOM (Digital Imaging and Communications in Medicine) format in a PACS (Picture Archiving and Communication Systems) adopted in a department of radiology, and medical image data in a Non-DICOM format such as a JPEG (Joint Photographic Experts Group) format, a Tiff (Tagged Image File Format), and an Analyze format, stores the received medical image data in a memory of the apparatus itself, and manages the medical image data.

The VNA 110 stores two-dimensional medical image data and three-dimensional medical image data (volume data) in the memory of the apparatus itself and manages the medical image data. Further, the VNA 110 can also store data with a vendor unique standard such as examination reports in the memory of the apparatus itself and manages the data. The VNA 110 is realized by, for example, a computer device such as a server or a workstation.

The AI service server 120 is a server device that provides an API (Application Programming Interface) for algorithms for machine learning and deep learning. Specifically, the AI service server 120 receives learning data including input data and teaching data based on the input data via the network 200 and generates a learned model by machine learning using the received learning data. The AI service server 120 inputs the input data into the generated learned model and outputs output data based on the learned model.

Figure 2:
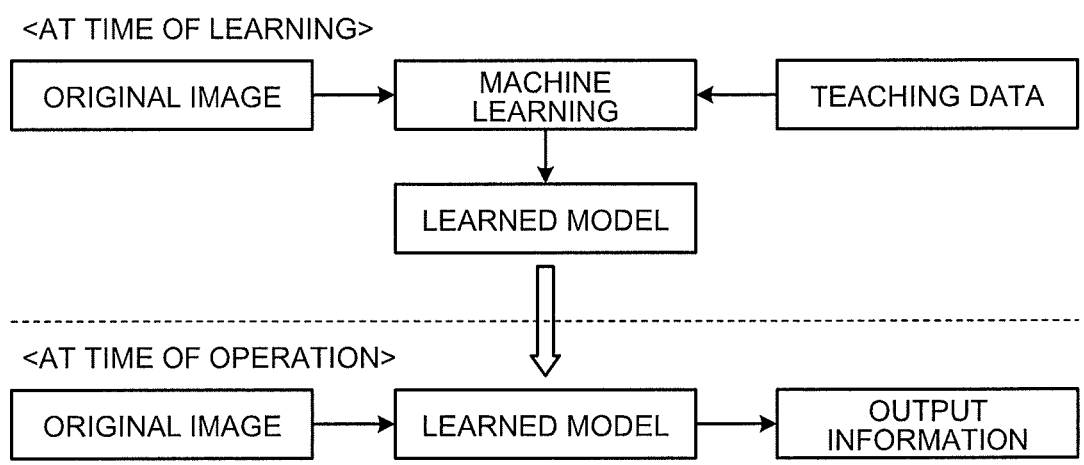
FIG. 2 is a diagram illustrating processing at the time of learning and at the time of operation performed by an AI service server according to the present embodiment.

The AI service server 120 according to the present embodiment provides the API for an arbitrary image processing algorithm. Processing in the AI service server 120 is described by using an example of constructing an algorithm for segmenting a brain into anatomical regions or physiological regions from a T1-weighted image (T1W) of a head region. FIG. 2 is a diagram illustrating processing at the time of learning and at the time of operation performed by the AI service server 120 according to the present embodiment.

For example, as illustrated in an upper part of FIG. 2, at the time of learning, the AI service server 120 generates a learned model that outputs a segmentation result based on an original image of a subject by learning a relation between the T1-weighted images (original image) of the head region collected from the subject and the segmentation result (teaching data) acquired by performing segmentation of the original image. The teaching data is, for example, a result of anatomical or physiological segmentation performed by a doctor with respect to the brain included in the original image.

That is, the AI service server 120 according to the present embodiment generates a learned model that outputs a segmentation result based on the original image by learning a relation among the original image, an image feature amount acquired by analyzing the original image, and image feature amounts of regions acquired by the segmentation of the original image.

The image feature amount here is a numerical value quantitatively indicating features of an image. For example, the image feature amount is an analytical value acquired by performing texture analysis or the like using the original image. The image feature amount is derived every time the original image and the teaching data are transmitted and is accumulated in a DB (DATABASE) in the AI service server 120, by associating the original image with the teaching data.

The AI service server 120 acquires plural pieces of learning data (the original image, the teaching data, and the image feature amount) by referring to the DB. The AI service server 120 inputs the acquired original image, teaching data, and image feature amount to a machine learning engine in the apparatus itself to perform machine learning.

The machine learning engine decides a parameter most appropriate for segmentation by comparing, for example, an image feature amount of the input original image with an image feature amount in the segmented region. The machine learning engine decides the most appropriate parameter by using various kinds of algorithms of, for example, deep learning, neural networks, logistic regression analysis, non-linear discrimination analysis, a support vector machine (SVM), random forest, and Naive Bayes.

As a result of such machine learning, the AI service server 120 generates a learned model that outputs a segmentation result based on the original image. The AI service server 120 memorizes the generated learned model in the memory of the apparatus itself. At this time, when a learned model generated previously has been already memorized in the memory, the AI service server 120 replaces the memorized learned model by a newly generated learned model.

Meanwhile, for example, as illustrated in a lower part of FIG. 2, at the time of operation, the AI service server 120 receives the T1-weighted images (original image) collected from the head region of the subject, and inputs the received T1-weighted images to the learned model to output a segmentation result (output information).

Specifically, the AI service server 120 receives the original image to be segmented, which is transmitted from another device on the network 200. The AI service server 120 performs analysis processing such as texture analysis to the acquired original image to derive an image feature amount.

Thereafter, the AI service server 120 inputs the original image and the image feature amount to the learned model, to estimate a segmentation result of the anatomical region or the physiological region included in the brain of the original image. The AI service server 120 transmits an estimated result to the other device that has transmitted the original image.

Referring back to FIG. 1, the medical image processing apparatus 130 acquires medical image data from the VNA 110 and performs various types of image processing by using the acquired medical image data. Further, for example, the medical image processing apparatus 130 transmits a processing result of the medical image data to the AI service server 120 as learning data. Further, for example, the medical image processing apparatus 130 transmits the medical image data to the AI service server 120 to acquire output information of the learned model. For example, the medical image processing apparatus 130 is realized by a computer device such as a server, a workstation, a personal computer, or a tablet terminal.

As illustrated in FIG. 1, the medical image processing apparatus 130 includes a communication interface 131, a memory 132, an input interface 133, a display 134, and processing circuitry 135.

The communication interface 131 is connected to the processing circuitry 135 and controls communication performed between the medical image processing apparatus 130 and respective systems. Specifically, the communication interface 131 receives various types of information from the respective systems and outputs the received information to the processing circuitry 135. For example, the communication interface 131 is realized by a network card, a network adapter, an NIO (Network Interface Controller), and the like.

The memory 132 is connected to the processing circuitry 135 and memorizes therein various types of data. For example, the memory 132 memorizes therein the medical image data received from the VNA 110 and output information acquired from the AI service server 120. Further, the memory 132 memorizes therein various programs for realizing various functions, which are read and executed by the processing circuitry 135. For example, the memory 132 is realized by a semiconductor memory elements such as a RAM (Random Access Memory) or a flash memory, a hard disk, an optical disk, and the like.

The input interface 133 is connected to the processing circuitry 135 and receives various instructions and an input operation of information from an operator. Specifically, the input interface 133 converts the input operation received from the operator to an electric signal and outputs the electric signal to the processing circuitry 135. The input interface 133 is realized, for example, by a trackball, a switch button, a mouse, a keyboard, a touch pad on which an input operation is performed by touching an operation surface thereof, a touch screen in which a display screen and a touch pad are integrated, a contactless input circuit using an optical sensor, a voice input circuit, and the like. In the present specification, the input interface 133 is not limited to the one including a physical operation parts such as a mouse or a keyboard. For example, a processing circuit of an electric signal that receives an electric signal corresponding to an input operation from an external input device provided separately from the apparatus and outputs the electric signal to a control circuit is also included in the example of the input interface 133.

The display 134 is connected to the processing circuitry 135 and displays thereon various types of information and images. Specifically, the display 134 converts the information and image data transmitted from the processing circuitry 135 to an electric signal for display and outputs the electric signal. For example, the display 134 is realized by a liquid crystal monitor, a CRT (Cathode Ray Tube) monitor, a touch panel, and the like.

The processing circuitry 135 controls the operation of the medical image processing apparatus 130 in response to an input operation received from the operator via the input interface 133. For example, the processing circuitry 135 is realized by a processor.

The configuration of the medical image processing system 100 according to the present embodiment has been described above. For example, the medical image processing system 100 according to the present embodiment is configured by the VNA 110 and the medical image processing apparatus 130 arranged in medical institutions such as a hospital and a clinic, and the AI service server 120 arranged on an external network. In such a configuration, the medical image processing system 100 enables to reduce the labor required for extraction of the learning data.

As described above, the AI service server 120 receives the learning data and provides an API for an algorithm related to image processing. To construct a more accurate (or more versatile) algorithm, it is required to collect many pieces of learning data so that the AI service server 120 performs further machine learning.

However, when an algorithm related to image processing is to be constructed, because there is a piece of appropriate medical image data for each intended algorithm, and it is not so easy to extract the piece of appropriate medical image data for the intended algorithm among the many pieces of medical image data. For example, when a segmentation algorithm of the brain intended for T1-weighted images of the head region is made to be more accurate (or more versatile), medical image data in which a region and an image type are respectively "head region" and "T1-weighted image", which satisfies restrictions of the algorithm (for example, the image quality and detailed regions included in an image) is extracted from the many pieces of medical image data, and the time and labor are required for extracting the medical image data in many cases.

Therefore, according to the present embodiment, when extracting learning data from many pieces of medical image data managed in the VNA 110, the medical image processing apparatus 130 in the medical image processing system 100 performs image analysis with respect to the plural pieces of collected medical image data, and extracts medical image data having an attribute common to teaching data used for generation of a learned model as a candidate of the teaching data of the learned model based on an analysis result, thereby reducing the labor required for extraction of the learning data. According to the medical image processing apparatus 130, appropriate learning data can be easily extracted not only from the medical image data in the DICOM format including various types of information in a header, but also from the medical image data in the Non-DICOM format such as the Tiff or the JPEG format.

The medical image processing apparatus 130 according to the present embodiment is described below in detail. As illustrated in FIG. 1, the processing circuitry 135 of the medical image processing apparatus 130 performs a control function 135a, an analysis function 135b, an extraction function 135c, an acquisition function 135d, and a decision function 135e. The processing circuitry 135 here is an example of processing circuitry.

The control function 135a executes control so as to perform processing in response to various requests input via the input interface 133. For example, the control function 135a controls transmission and reception of medical image data and the like via the communication interface 131, storage of information in the memory 132, and display of information (for example, a display image and analysis results) on the display 134.

For example, the control function 135a acquires plural pieces of medical image data from the VNA 110 and stores the medical image data in the memory 132. Further, for example, the control function 135a executes control so as to display a GUI for selecting various conditions at the time of extracting the learning data from the plural pieces of medical image data acquired from the VNA 110 and processing results obtained by the respective functions on the display 134. Details of the display contents displayed by the control function 135a are described later.

The medical image data acquired by the control function 135a is two-dimensional medical image data or three-dimensional medical image data according to an intended algorithm. For example, when a processing target of the algorithm of a target learned model is volume data, the control function 135a acquires three-dimensional medical image data from the VNA 110. Meanwhile, when the processing target of the algorithm of the target learned model is two-dimensional medical image data, the control function 135a acquires two-dimensional medical image data from the VNA 110, or extracts and acquires two-dimensional medical image data (for example, one slice of volume data) from the volume data stored in the VNA 110.

As to whether the processing target is two-dimensional medical image data or three-dimensional medical image data may be designated by an operator or may be decided by the control function 135a according to the algorithm of the target learned model. When the processing target is designated by the operator, the control function 135a displays, for example, a GUI for selecting two-dimensional medical image data or three-dimensional medical image data on the display 134 and receives a designating operation by the operator via the input interface 133. Further, when the control function 135a is to decide whether the processing target is two-dimensional medical image data or three-dimensional medical image data according to the algorithm of the target learned model, for example, the memory 132 memorizes therein beforehand correspondence information in which algorithms and pieces of data information to be processed (whether the data is two-dimensional or three-dimensional) are associated with each other. The control function 135a refers to the correspondence information in the memory 132 to decide whether the medical image data is two-dimensional or three-dimensional based on the data information corresponding to the algorithm of the target learned model.

The analysis function 135b performs image analysis with respect to the plural pieces of collected medical image data. Specifically, the analysis function 135b performs analysis using the learned model or image processing for specifying an image type with respect to the plural pieces of collected medical image data. For example, the analysis function 135b performs image analysis for specifying a region and image analysis for specifying an image type with respect to the plural pieces of medical image data acquired from the VNA 110 and memorized in the memory 132. Further, the analysis function 135b performs analysis for determining whether an image is appropriate for an original image in the learning data. The analysis function 135b then adds an analysis result to the respective pieces of medical image data and stores the medical image data added with the analysis result in the memory 132.

The analysis function 135b specifies a region included in the respective pieces of medical image data, for example, by performing analysis based on an anatomical landmark or the like. As an example, the analysis function 135b extracts an anatomical landmark from the respective pieces of medical image data and compares the extracted anatomical landmark with an anatomical landmark for each region, to specify a region (for example, a head region, a breast region, an abdominal region, a lower limb, or the like) included in the respective pieces of medical image data.

The analysis function 135b then specifies the image type by analysis using the learned model or the image processing. The analysis for specifying respective image types from "T1-weighted image (T1W)", "T2-weighted image (T2W)", "CT (Computed Tomography) image", "FLAIR (FLuid- Attenuated Inversion Recovery) image", and "DWI (Diffusion Weighted Image) image" obtained by taking images of the brain is described as an example.

For example, when the learned model is used, a learned model using information of a region indicating a characteristic signal value in the respective image types is constructed beforehand. For example, a learned model in which a signal value and an image type are handled as learning data is generated by using such characteristics that "T1-weighted image: CSF (cerebrospinal fluid) indicates a low signal", "T2-weighted image: CSF indicates a high signal", "FLAIR image: CSF indicates a low signal in T2 W", "DWI image: there is much noise as compared with other images", and "CT image: the brainpan indicates a high signal". The learned model may be constructed by the AI service server 120 or constructed by the medical image processing apparatus 130. For example, the analysis function 135b specifies the image type of each of respective pieces of medical image data by inputting respective pieces of medical image data in which a region is specified as a head region into the learned model described above.

Further, when the image processing is used, the analysis function 135b can classify the image types described above by using an existing algorithm. As an example, the analysis function 135b can classify "T1-weighted image", "T2-weighted image", and "FLAIR image" by applying Voxel Based Morphometry (VBM). For example, the analysis function 135b performs anatomical standardization with respect to each of the respective pieces of medical image data and segments the medical image data into a gray matter, a white matter, and CSF (cerebrospinal fluid) by using cluster analysis and a prior probability image. The analysis function 135b specifies "T1-weighted image", "T2-weighted image", and "FLAIR image" based on a distribution of the signal values in the segmented gray matter, white matter, and CSF (cerebrospinal fluid).

Further, the analysis function 135b performs profile extraction with respect to each of the respective medical image data and specifies "CT image" according to whether there is a high signal region in the outside of the head region (a brainpan). Further, the analysis function 135b calculates an S/N (signal-to-noise) ratio in each piece of medical image data, and compares the calculated S/N ratio with a predetermined threshold to specify the medical image data having the S/N ratio lower than the threshold as "DWI image".

As described above, when the analysis function 135b performs analysis processing with respect to each piece of medical image data, the extraction function 135c extracts a candidate of the learning data based on an analysis result. Specifically, the extraction function 135c extracts medical image data having an attribute common to the teaching data used for generation of the learned model from the plural pieces of collected medical image data as the candidate of the teaching data of the learned model, based on the analysis result obtained by the analysis function 135b.

More specifically, the extraction function 135c respectively discriminates a feature included in the plural pieces of medical image data based on the analysis result of the image analysis, and extracts medical image data having an attribute common to the teaching data of the learned model from the plural pieces of medical image data based on a discrimination result. Here, the extraction function 135c extracts medical image data satisfying criteria to be used for the learned model as a candidate of the teaching data. An example of processing performed by the extraction function 135c is described below.

For example, the extraction function 135c first acquires a region and an image type of the medical image data to be extracted by referring to an original image of the teaching data having used as the learning data of the target learned model, and extracts the medical image data of the acquired region and image type. As an example, the extraction function 135c acquires "region: head region (brain)" and "image type: T1W". The extraction function 135c then extracts "T1W of the head region", the same as the acquired region and image type from the plural pieces of medical image data memorized in the memory 132 by referring to the analysis result obtained by the analysis function 135b.

Further, the extraction function 135c also extracts pieces of medical image data appropriate for the learning data from the pieces of extracted medical image data. For example, the extraction function 135c extracts plural pieces of medical image data of the image type common to the teaching data and extracts medical image data having an attribute common to the teaching data from the pieces of extracted medical image data, based on at least one of the image quality, the degree of similarity to the original image of the teaching data, and restrictions to be used in the learned model.

When a piece of medical image data appropriate for the learning data is further extracted, an extraction target can be changed according to whether the algorithm of the learned model is set to have higher accuracy or higher versatility. That is, the extraction function 135c can switch extraction determination according to whether the algorithm of the learned model is set to have higher accuracy or higher versatility.

As to whether the algorithm of the learned model is set to have higher accuracy or higher versatility can be arbitrarily set by an operator. The operator can select whether the algorithm of the learned model is set to have higher accuracy or higher versatility by arbitrarily selecting respective extraction processing described below. In this case, for example, the control function 135a displays a GUI related to respective extraction processing described below on the display 134, and the operator selects which extraction processing is to be performed according to which threshold determination via the input interface 133.

First, extraction processing when the algorithm of the learned model is set to have higher accuracy is described. In this case, for example, the extraction function 135c respectively calculates the S/N ratio of the respective pieces of medical image data extracted based on the region and the image type and excludes medical image data in which the calculated S/N ratio has not reached a predetermined threshold from the extraction target. That is, the extraction function 135c extracts only the medical image data having predetermined image quality, among the pieces of medical image data extracted based on the region and the image type. The threshold to be set with respect to the S/N ratio may be set respectively for each target learned model or a representative value may be set as the threshold.

Further, for example, the extraction function 135c calculates the degree of similarity between the medical image data extracted based on the region and the image type and the original image of the teaching data and extracts medical image data whose degree of similarity has reached a predetermined value. As an example, the extraction function 135c calculates mutual information (MI) between a signal value of the extracted medical image data and a signal value of the original image of the teaching data, and when the calculated mutual information has not reached a predetermined threshold, the extracted medical image data is excluded from the extraction target.

Further, for example, the extraction function 135c extracts a piece of medical image data appropriate for the learning data by using, as restrictions to be used for the learned model, whether a section is appropriate, whether a slice pitch is appropriate, whether an artifact is not too large, whether all the target regions are included in the medical image data, and whether a tumor is included in the medical image data.

As an example, regarding a segmentation algorithm for the brain, the extraction function 135c further extracts a piece of medical image data appropriate for the learning data among the pieces of extracted medical image data, based on such judgment criteria that "sagittal section is appropriate", "image in which slice pitch is equal to or smaller than predetermined pitch is appropriate", "image in which artifact is not too large is appropriate", "image in which all target regions are included in medical image data is appropriate", and "image that does not include tumor is appropriate".

Further, in the extraction processing when the algorithm of the learned model is set to have higher versatility, for example, a threshold at the time of extracting the medical image data based on the degree of similarity between the medical image data extracted based on the region and the image type and the original image of the teaching data is set to be lower than the case where the algorithm of the learned model is set to have higher accuracy. The extraction function 135c extracts medical image data appropriate for the learning data based on the set threshold.

Further, for example, in the extraction processing when the algorithm of the learned model is set to have higher versatility, the extraction function 135c extracts the medical image data without using a restriction of the imaged section. That is, the extraction function 135c extracts any of a sagittal section, an axial section, and a coronal section as the appropriate medical image data.

The extraction examples described above are examples only, and the extraction function 135c can extract medical image data appropriate for the learning data according to setting performed by an operator, and according to other various conditions and various combinations.

The acquisition function 135d acquires output data by inputting medical image data having an attribute common to the teaching data into the learned model as input data. Specifically, the acquisition function 135d transmits the medical image data appropriate for the learning data extracted by the extraction function 135c to the AI service server 120 as the input data of the learned model. The AI service server 120 transmits the output data acquired by inputting the input data received from the acquisition function 135d into the learned model to the acquisition function 135d. The acquisition function 135d stores the output data received from the AI service server 120 in the memory 132 as primary teaching data.

The decision function 135e decides the input data and the output data as the learning data of the learned model. Specifically, the decision function 135e decides processed medical image data obtained by applying correction processing to the primary teaching data by an operator as the teaching data, and decides the teaching data and the original image of the teaching data (the medical image data transmitted to the AI service server 120) as the learning data. The decision function 135e then transmits the decided learning data to the AI service server 120 so that the AI service server 120 performs machine learning using the decided learning data.

The correction processing performed by the operator with respect to the primary teaching data is performed based on, for example, display information displayed on the display 134. That is, the control function 135a displays information related to the primary teaching data on the display 134. For example, the control function 135a executes control to display, on the display 134, at least one of the score based on the extraction processing performed by the extraction function 135c, collected date and time of the pieces of medical image data, an acquisition status of the primary teaching data by the acquisition function 135d, and a comparison result between the teaching data used for generation of the learned model and the primary teaching data, along with the primary teaching data.

The input interface 133 receives an operation with respect to the display information from the operator. That is, the operator judges whether the primary teaching data is to be used as the learning data and whether correction is to be performed when the primary teaching data is used as the learning data, based on various types of display information displayed on the display 134, decides the primary teaching data to be used as the learning data, and performs an operation to set the decided primary teaching data as the learning data. The decision function 135e decides the learning data based on the operation performed by the operator and transmits the decided learning data to the AI service server 120.

As described above, the medical image processing apparatus 130 according to the present embodiment analyzes the medical image data managed by the VNA 110 to extract a piece of medical image data to be a candidate of the learning data, and applies the extracted medical image data to the learned model, thereby acquiring the primary teaching data. The medical image processing apparatus 130 presents the primary teaching data to the operator and decides medical image data determined to be appropriate for the teaching data by the operator as the teaching data. The medical image processing apparatus 130 further transmits the decided teaching data and the original image of the teaching data to the AI service server 120.

Figure 3:
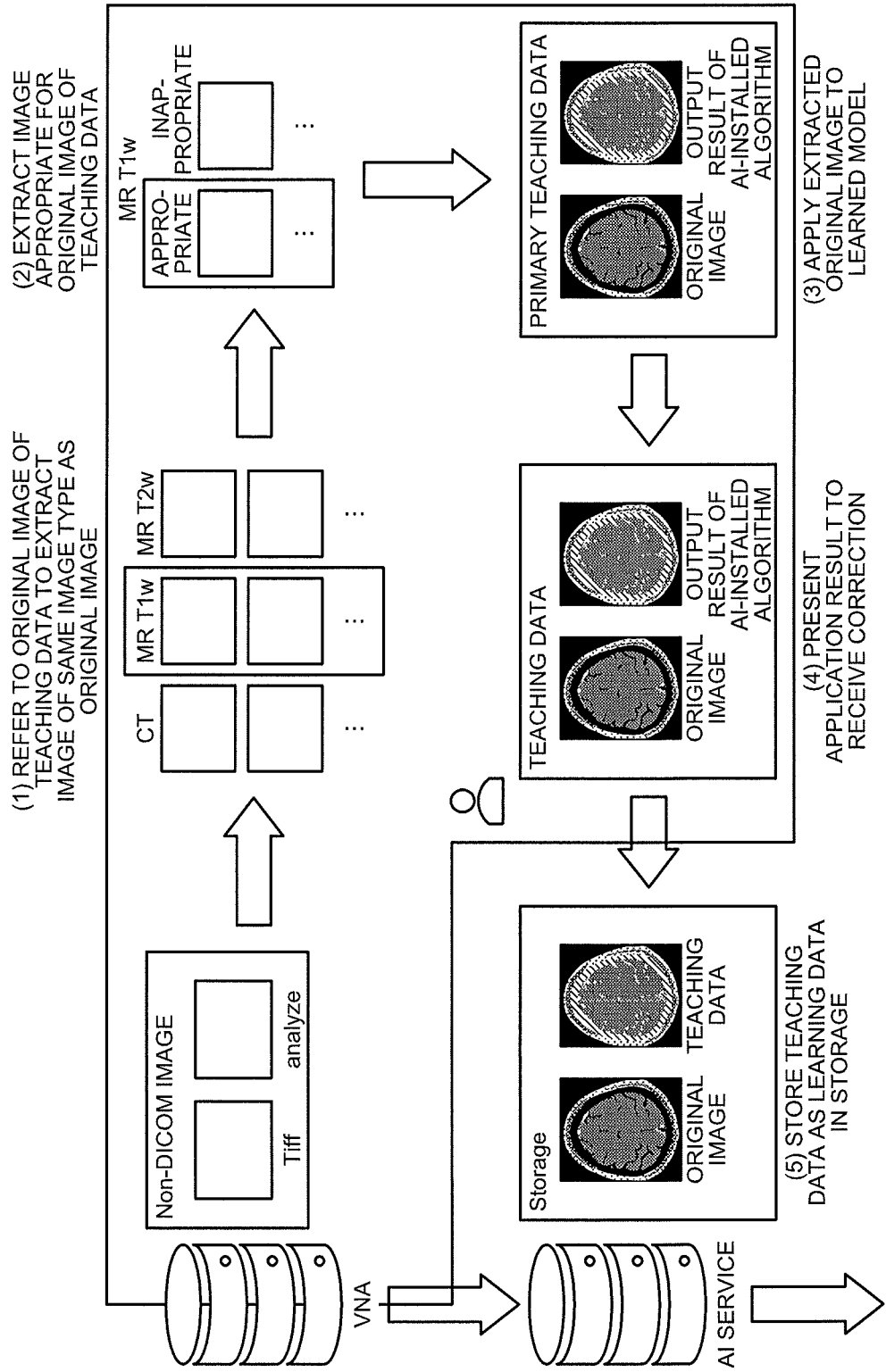
FIG. 3 is an explanatory diagram of an example of processing performed by a medical image processing apparatus according to the present embodiment.

An example of processing performed by the medical image processing apparatus 130 is described below with reference to FIG. 3. FIG. 3 is an explanatory diagram of an example of processing performed by the medical image processing apparatus 130 according to the present embodiment. FIG. 3 illustrates an example in which the medical image processing apparatus 130 extracts learning data appropriate for an algorithm of a learned model of brain segmentation using the T1W of the head region from the Non-DICOM images stored in the VNA 110.

As illustrated in FIG. 3, in the medical image processing apparatus 130, the extraction function 135c (1) refers to an original image of teaching data to extract an image of the image type same as the original image. In this case, the analysis function 135b performs analysis processing for specifying a region and an image type, for example, with respect to Non-DICOM images in the Tiff or in the analyze format stored in the VNA 110. The extraction function 135c extracts T1Ws in which a head region is imaged by an MRI device among the Non-DICOM images based on an analysis result obtained by the analysis function 135b.

The extraction function 135c (2) extracts medical image data appropriate for the original image of teaching data from the T1Ws of the head region extracted in (1). That is, the extraction function 135c extracts medical image data appropriate for the original image of the teaching data based on the image quality and the degree of similarity analyzed by the analysis function 135b, and restrictions in the learned model. Here, the extraction function 135c extracts medical image data satisfying conditions selected by an operator as the medical image data appropriate for the original image of the teaching data.

The acquisition function 135d transmits the medical image data appropriate for the original image of the teaching data extracted by the extraction function 135c to the AI service server 120, (3) thereby applying the extracted original image to the learned model to acquire primary teaching data. That is, the acquisition function 135d applies the T1W of the head region appropriate for the original image of the teaching data to the learned model of the brain segmentation, to acquire a segmentation result (an output result of an AI-installed algorithm).

Here, the acquisition function 135d can perform image processing to the medical image data to be transmitted to the AI service server 120. For example, in the case of a learned model of brain segmentation using the T1W of the head region, if the brain included in the T1W of the head region to be transmitted is quite different from a general shape, an output error may occur. For example, since the size of the brain atrophies with age, the extracted T1W as it is may cause an output error. Therefore, the acquisition function 135d can perform preprocessing for adjusting the scale of the image with respect to the T1W before transmitting the T1W of the head region to the AI service server 120 to align the size of the image of the brain uniformly and transmit the T1W to the AI service server 120.

The control function 135a (4) presents an application result to the learned model to the operator and receives correction from the operator. That is, the control function 135a displays the primary teaching data acquired by the acquisition function 135d on the display 134 to receive correction by the operator. Here, the control function 135a can present an analysis result obtained by the analysis function 135b to the operator, along with the segmentation result obtained by the AI service server 120.

Figure 4:
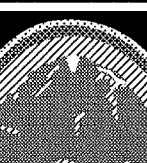
FIG. 4 is a diagram illustrating an example of display information to be displayed by a control function according to the present embodiment.

FIG. 4 is a diagram illustrating an example of display information to be displayed by the control function 135a according to the present embodiment. For example, the control function 135a displays display information in which "score", "date and time", "presence of error", and "test result" are associated with "primary teaching data" on the display 134, as illustrated in FIG. 4.

Here, "primary teaching data" indicates a result of brain segmentation performed by the AI service server 120. Further, "score" indicates a result of adding a score to the analysis result obtained by the analysis function 135b. For example, when it is determined whether the medical image data is appropriate for the learning data, "score" is added according to the number of items satisfying the conditions. As an example, "score" is respectively calculated according to conditions for setting the algorithm of the learned model to have higher accuracy and conditions for setting the algorithm of the learned model to have higher versatility.

Further, "date and time" indicates the date and time when the original image of the primary teaching data has been collected. "test result" indicates a test result when the teaching data of the learning data (the segmentation result) used for machine learning by the AI service server 120 is compared with the primary teaching data. As "test result", for example, mean values of volume values and area values of segmented regions and SD (Standard Deviation) in the teaching data used for the machine learning are calculated, and it is indicated whether the volume values and the area values in the segmentation result in the primary teaching data are within 2SD. Further, as "test result", for example, a contrast value among respective segmented regions is indicated.

The "score" and "test result" described above are calculated, for example, by the analysis function 135b and displayed on the display 134 by the control function 135a. Further, the control function 135a can display a GUI for enabling arbitrary rearrangement of "score", "date and time", "presence of error", and "test result" in an ascending order or a descending order, as illustrated in FIG. 4.

The operator refers to the display information as illustrated in FIG. 4 to decide the medical image data to be adopted as the learning data. Specifically, the operator first decides the primary teaching data to be adopted based on "score", "date and time", "presence of error", and "test result". The operator then refers to the adopted primary teaching data (the segmentation result) to determine whether correction is required for a region of the respective classified portions (for example, a gray matter, a white matter, and CSF). When determining that correction is required, the operator corrects the region via the input interface 133 to generate teaching data.

Thereafter, the operator performs a decision operation for deciding the corrected teaching data and the original image of the teaching data as the learning data. The decision function 135e transmits the corresponding corrected teaching data and the original image of the teaching data to the AI service server 120, according to the decision operation performed by the operator.

As described above, the medical image processing apparatus 130 extracts medical image data that becomes a candidate of the learning data and applies the extracted medical image data to the learned model to acquire the primary teaching data, and decides the teaching data in response to the operator's operation with respect to the primary teaching data. The medical image processing apparatus 130 transmits the decided teaching data to the AI service server 120 so that the AI service server 120 is caused to update the learned model.

The medical image processing apparatus 130 here can update the learned model for each condition at the time of extracting a piece of appropriate medical image data and for each operator who has performed an operation with respect to the primary teaching data. In such a case, when transmitting the learning data to the AI service server 120, the decision function 135e transmits the learning data by adding an identifier thereto so as to be able to identify the condition or the operator, so that the AI service server 120 is caused to update the learned model for each condition or for each operator. In this case, the AI service server 120 manages the learned model for each condition or for each operator.

The respective processing functions provided in the processing circuitry 135 of the medical image processing apparatus 130 have been described above. When the processing circuitry 135 is realized by a processor, the respective processing functions provided in the processing circuitry 135 are memorized in the memory 132 in a format of a program executable by a computer. The processing circuitry 135 reads the respective programs from the memory 132 and executes the respective programs, to realize the functions corresponding to the respective programs. In other words, the processing circuitry 135 in a state of having read the respective programs has the respective functions illustrated in the processing circuitry 135 in FIG. 1. It has been described that respective processing functions are realized by a single processor with reference to FIG. 1. However, a plurality of independent processors can be combined to constitute a processing circuit, and the respective processors can realize each function by executing each program. Further, the processing functions provided in the processing circuitry 135 can be realized by being distributed appropriately to a plurality of processing circuits or integrated in a single processing circuit. In the example illustrated in FIG. 1, it is described that a single memory 132 memorizes the programs corresponding to the respective processing functions. However, such a configuration is also possible that a plurality of memory circuits can be arranged in a distributed manner, and the processing circuit reads a corresponding program from an individual memory circuit.

A processing procedure by the medical image processing apparatus 130 is described next. FIG. 5 is a flowchart illustrating a processing procedure performed by the medical image processing apparatus 130 according to the present embodiment. Here, Step S101 to Step S104 in FIG. 5 are steps realized by calling up programs corresponding to the analysis function 135*b* and the extraction function 135*c* from the memory 132 and executing the programs by the processing circuitry 135. Step S105 in FIG. 5 is a step realized by calling up a program corresponding to the acquisition function 135*d* from the memory 132 and executing the program by the processing circuitry 135. Step S106 in FIG. 5 is a step realized by calling up a program corresponding to the control function 135*a* from the memory 132 and executing the program by the processing circuitry 135. Further, Step S107 to Step S110 are steps realized by calling up a program corresponding to the decision function 135*e* from the memory 132 and executing the programs by the processing circuitry 135.

As illustrated in FIG. 5, in the medical image processing apparatus 130, the processing circuitry 135 first determines whether extraction processing of learning data has been started (Step S101). Here, when the extraction processing is started (YES at Step S101), the processing circuitry 135 refers to an original image of medical image data used for teaching data (Step S102) to analyze pieces of medical image data registered in the VNA 110 and extract pieces of medical image data of the same image type as the original image (Step S103). Until the extraction processing is started, the processing circuitry 135 is in a standby state (NO at Step S101).

The processing circuitry 135 further extracts medical image data appropriate for the original image from the pieces of extracted medical image data based on an analysis result (Step S104). Thereafter, the processing circuitry 135 applies the extracted medical image data to a learned model (Step S105) and presents an output result to a user (Step S106) to determine whether correction has been received (Step S107).

When correction has been received (YES at Step S107), the processing circuitry 135 reflects a correction result (Step S108) and determines whether a registration operation has been received (Step S109). When correction has not been received (NO at Step S107), the processing circuitry 135 determines whether the registration operation has been received (Step S109).

When the registration operation has been received (YES at Step S109), the processing circuitry 135 transmits learning data to the AI service server 120 so that the AI service server 120 is caused to update and store the learned model (Step S110). On the other hand, when the registration operation has not been received (NO at Step S109), the processing circuitry 135 ends the processing.

As described above, according to the present embodiment, the analysis function 135*b* performs image analysis with respect to pieces of collected medical image data. The extraction function 135*c* extracts medical image data having an attribute common to the teaching data used for generation of the learned model from the pieces of collected medical image data as a candidate of the teaching data of the learned model, based on an analysis result obtained by the analysis function 135*b*. Therefore, the medical image processing apparatus 130 according to the present embodiment can extract a candidate of the teaching data of the learned model based on image information, thereby enabling to reduce the labor required for extracting the learning data from many pieces of medical image data.

Further, according to the present embodiment, the analysis function 135*b* performs analysis using a learned model or image processing for specifying the image type with respect to the pieces of collected medical image data. The extraction function 135*c* extracts plural pieces of medical image data of an image type common to the teaching data based on an analysis result obtained by the analysis function 135*b* and extracts medical image data having an attribute common to the teaching data from the pieces of extracted medical image data, based on at least one of the image quality, the degree of similarity to the original image of the teaching data, and restrictions to be used for the learned model. Therefore, the medical image processing apparatus 130 according to the present embodiment can easily extract learning data appropriate for the target learned model.

Further, according to the present embodiment, the acquisition function 135*d* acquires output data by inputting medical image data having an attribute common to the teaching data to the learned model as input data. The decision function 135*e* decides the input data and the output data as the learning data of the learned model. Therefore, the medical image processing apparatus 130 according to the present embodiment can reduce the labor required for extracting the teaching data of the learned model.

Further, according to the present embodiment, the control function 135*a* executes control so that the output data is displayed on the display 134. The input interface 133 receives a processing operation with respect to the output data displayed on the display 134. The decision function 135*e* decides the input data and the processed output data as the learning data of the learned model. Therefore, the medical image processing apparatus 130 according to the present embodiment can easily extract teaching data having higher reliability.

Further, according to the present embodiment, the decision function 135*e* transmits the input data and the processed output data to the AI service server 120 that provides an algorithm of the learned model so that the AI service server 120 is caused to update the learned model. Therefore, the medical image processing apparatus 130 according to the present embodiment can easily perform update of the learned model.

Further, according to the present embodiment, the control function 135*a* executes control to display at least one of the score based on the extraction processing performed by the extraction function 135*c*, the collected date and time of the pieces of medical image data, an acquisition status of the output data by the acquisition function 135*d*, and a comparison result between the teaching data used for generation of the learned model and the output data on the display 134, along with the output data. Therefore, the medical image processing apparatus 130 according to the present embodiment can easily extract medical image data appropriate for the target learned model.

Further, according to the present embodiment, the acquisition function 135d acquires the output data by inputting medical image data having an attribute common to the teaching data to the learned model, after performing image deformation (for example, processing to align the size of the brain). Therefore, the medical image processing apparatus 130 according to the present embodiment can prevent an error when acquiring the primary teaching data.

Other Embodiments

The embodiment described above can be also carried out with appropriate modifications by changing a part of the configurations or functions of the medical image processing apparatus 130. In the following descriptions, several modifications according to the embodiment described above are described as other embodiments. In the following descriptions, points different from the embodiment described above are mainly described and detailed descriptions of the points common to the contents already described are omitted. The respective embodiments described below can be carried out individually or carried out while being combined with one another appropriately.

Other Embodiment—1

For example, in the embodiment described above, there has been described an example in which, if an error has occurred at the time of acquiring primary teaching data, the primary teaching data is excluded from a target. However, the embodiment is not limited thereto, and a result when the error has occurred is fed back so as to be reflected in the extraction processing performed by the extraction function 135c.

In such a case, for example, the acquisition function 135d causes the memory 132 to memorize therein the medical image data stored in the memory 132 in such a manner that a piece of medical image data, to which an error is notified in an output result received from the AI service server 120, is memorized in association with a fact that an error is notified. The extraction function 135c accumulates pieces of attribute information of the medical image data in which an error has occurred in acquisition of the output data by the acquisition function 135d and the medical image data having the accumulated attribute information is excluded from the extraction target. For example, the extraction function 135c calculates an image feature amount of the medical image data associated with the fact that an error is notified and accumulates the information of the calculated image feature amount in the memory 132. Subsequently, at the time of extracting the medical image data appropriate for the learning data, the extraction function 135c excludes the medical image data having the accumulated image feature amount from the extraction target. With this configuration, the medical image processing apparatus 130 can automatically extract medical image data appropriate for the learning data.

Other Embodiment—2

Further, for example, in the above embodiment, there has been described a case where learning data of a learned model generated based on medical image data is extracted. However, the embodiment is not limited thereto, and for example, such a case is also applicable that other pieces of subject information such as ECG (Electrocardiogram) are used.

Other Embodiment—3

Further, in the above embodiment, there has been described a case where the medical image processing apparatus 130 is installed in medical institutions such as a hospital and a clinic. However, the embodiment is not limited thereto. For example, the medical image processing apparatus 130 can be installed in a place separate from medical institutions and can be communicably connected to the VNA 110 that is installed in one or a plurality of medical institutions via the network 200.

In this case, for example, the medical image processing apparatus 130 acquires medical image data from the VNA 110 that is installed in respective medical institutions via the network 200 and extracts learning data.

Other Embodiment—4

Further, in the above embodiment, there has been described a case where the learning data extracted by the medical image processing apparatus 130 is transmitted to the AI service server 120 to generate a learned model. However, the embodiment is not limited thereto, and for example, a learned model can be generated by the medical image processing apparatus 130.

Other Embodiment—5

Further, in the above embodiment, there has been described a case where the medical image processing apparatus 130 performs the control function 135a, the analysis function 135b, the extraction function 135c, the acquisition function 135d, and the decision function 135e. However, the embodiment is not limited thereto, and for example, the respective functions are performed separately by a plurality of devices included in the medical image processing system 100.

Other Embodiment—6

Further, in the above embodiment, there has been described a case where a control unit, an analysis unit, an extraction unit, an acquisition unit, and a decision unit in the present specification are realized respectively by the control function 135a, the analysis function 135b, the extraction function 135c, the acquisition function 135d, and the decision function 135e of the processing circuitry 135. However, the embodiment is not limited thereto. For example, other than respectively realizing the control unit, the analysis unit, the extraction unit, the acquisition unit, and the decision unit in the present specification by the control function 135a, the analysis function 135b, the extraction function 135c, the acquisition function 135d, and the decision function 135e described in the embodiment, it is also possible that these functions are realized by only hardware or a combination of hardware and software.

The word "processor" used in the above descriptions means a CPU (Central Processing Unit), a GPU (Graphics Processing Unit), or a circuit such as an application specific integrated circuit (ASIC) and a programmable logic device (for example, a simple programmable logic device (SPLD), a complex programmable logic device (CPLD), and a field programmable Gate Array (FPGA)). The processor reads and executes a program stored in the memory 132 to realize the respective functions. Instead of storing the program in the memory 132, the program can be directly installed in the circuit of the processor. In this case, the processor reads and executes the program installed in a circuit to realize the respective functions. Further, respective processors according to the present embodiment are not limited to a case of being configured as a single circuit, and can be configured as one processor by combining a plurality of independent circuits to realize the functions thereof.

The program to be executed by the processor (a medical image processing program) is provided by being incorporated in a ROM (Read Only Memory) or a memory circuit in advance. This program can be recorded and provided in a computer-readable storage medium such as a CD (Compact Disk)-ROM, an FD (Flexible Disk), a CD-R (Recordable), and a DVD (Digital Versatile Disk) in a format installable or executable in the devices. Further, this program can be stored in a computer connected to a network such as the Internet and provided or distributed by downloading via a network. For example, this program can be constituted by a module including the functional units described above. As actual hardware, a CPU reads out the program from a storage medium such as a ROM and executes the program, thereby loading and generating respective modules on a main memory unit.

According to at least one of the embodiments described above, it is possible to reduce the labor required for extracting learning data.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image processing apparatus comprising:
   processing circuitry configured to
   specify teaching data having been used for generation of a learned model,
   perform image analysis with respect to pieces of collected medical image data,
   extract plural pieces of medical image data of an image type common to the teaching data from the pieces of collected medical image data based on the analysis result of the image analysis; and
   extract medical image data having an attribute common to the teaching data of the learned model from the pieces of extracted medical image data based on an analysis result of the image analysis, as a candidate of the teaching data of the learned model, including
   extract medical image data having an attribute common to the teaching data from the pieces of extracted medical image data, based on at least one of image quality, a degree of similarity to an original image of the teaching data, and restrictions to be used for the learned model.

2. The medical image processing apparatus according to claim 1, wherein the processing circuitry is configured to respectively discriminate a feature of each of the pieces of extracted medical image data based on the analysis result of the image analysis, and extract medical image data having an attribute common to the teaching data of the learned model from the pieces of extracted medical image data based on a discrimination result.

3. The medical image processing apparatus according to claim 1, wherein the processing circuitry is configured to extract medical image data satisfying criteria to be used for the learned model as a candidate of the teaching data.

4. The medical image processing apparatus according to claim 1, wherein the processing circuitry is configured to perform analysis using a learned model or image processing for specifying an image type with respect to the pieces of collected medical image data,
   extract the plural pieces of medical image data of the type common to the teaching data from the pieces of collected medical image data based on the analysis result of the image analysis for specifying the image type.

5. The medical image processing apparatus according to claim 1, wherein the processing circuitry is configured to
   acquire output data by inputting medical image data having an attribute common to the teaching data to the learned model as input data, and
   decide the input data and the output data as learning data of the learned model.

6. The medical image processing apparatus according to claim 5, wherein the processing circuitry is configured to
   execute control so as to display the output data on a display unit,
   receive a processing operation with respect to the output data displayed on the display unit, and
   decide the input data and the processed output data as the learning data of the learned model.

7. The medical image processing apparatus according to claim 6, wherein the processing circuitry is configured to transmit the input data and the processed output data to a provision apparatus that provides an algorithm of the learned model, so that the provision apparatus is caused to update the learned model.

8. The medical image processing apparatus according to claim 6, wherein the processing circuitry is configured to execute control so as to display, on the display unit, at least one of a score based on extraction processing, collected date and time of the pieces of medical image data, an acquisition status of the output data, and a comparison result between teaching data used for generation of the learned model and the output data, along with the output data.

9. The medical image processing apparatus according to claim 5, wherein the processing circuitry is configured to accumulate pieces of attribute information of medical image data in which an error has occurred at a time of acquiring the output data, and exclude medical image data having accumulated attribute information from an extraction target.

10. A medical image processing system comprising:
    processing circuitry is configured to
    specify teaching data used for generation of a learned model,
    perform image analysis with respect to pieces of collected medical image data,
    extract plural pieces of medical image data of an image type common to the teaching data from the pieces of collected medical image data based on the analysis result of the image analysis; and
    extract medical image data having an attribute common to the teaching data of the learned model from the pieces of extracted medical image data based on an analysis result of the image analysis, as a candidate of the teaching data of the learned model, including
    extract medical image data having an attribute common to the teaching data from the pieces of extracted medical image data, based on at least one of image quality, a degree of similarity to an original image of the teaching data, and restrictions to be used for the learned model.

11. A medical image processing method comprising:
    specifying teaching data used for generation of a learned model;
    performing image analysis with respect to pieces of collected medical image data;

extracting plural pieces of medical image data of an image type common to the teaching data from the pieces of collected medical image data based on the analysis result of the image analysis; and extracting medical image data having an attribute common to the teaching data of the learned model from the pieces of extracted medical image data based on an analysis result of the image analysis, as a candidate of the teaching data of the learned model, including extracting medical image data having an attribute common to the teaching data from the pieces of extracted medical image data, based on at least one of image quality, a degree of similarity to an original image of the teaching data, and restrictions to be used for the learned model.

* * * * *